(12) United States Patent
Murakami et al.

(10) Patent No.: US 6,998,432 B2
(45) Date of Patent: *Feb. 14, 2006

(54) ADHESIVE COMPOSITION FOR SKIN AND ADHESIVE TAPE OR SHEET FOR SKIN COMPRISING THE COMPOSITION

(75) Inventors: Yoshihide Murakami, Ibaraki (JP); Katsuhiro Okada, Ibaraki (JP)

(73) Assignee: Nitto Denko Corporation, Ibaraki (JP)

( * ) Notice: Subject to any disclaimer, the term of this patent is extended or adjusted under 35 U.S.C. 154(b) by 415 days.

This patent is subject to a terminal disclaimer.

(21) Appl. No.: 09/941,972

(22) Filed: Aug. 29, 2001

(65) Prior Publication Data

US 2002/0061948 A1    May 23, 2002

(30) Foreign Application Priority Data

Sep. 1, 2000 (JP) .............................. 2000-265365
Apr. 19, 2001 (JP) .............................. 2001-121313

(51) Int. Cl.
*C08K 5/10* (2006.01)
(52) U.S. Cl. ........................ 524/315; 525/317; 525/507
(58) Field of Classification Search ................ 524/315, 524/317, 507
See application file for complete search history.

(56) References Cited

U.S. PATENT DOCUMENTS

| | | | |
|---|---|---|---|
| 3,617,361 A * | 11/1971 | Reinhard et al. | 427/208.4 |
| 4,608,249 A | 8/1986 | Otsuka et al. | |
| 5,543,151 A | 8/1996 | Shirai et al. | |
| 5,783,209 A * | 7/1998 | Imamura et al. | 424/448 |
| 5,876,745 A * | 3/1999 | Muraoka et al. | 424/448 |
| 6,139,867 A * | 10/2000 | Muraoka et al. | 424/448 |
| 6,231,883 B1 * | 5/2001 | Inosaka et al. | 424/443 |
| 6,787,681 B1 * | 9/2004 | Murakami et al. | 602/57 |
| 2003/0224160 A1 * | 12/2003 | Murakami et al. | 428/343 |

FOREIGN PATENT DOCUMENTS

| | | |
|---|---|---|
| EP | 0369092 A2 A3 | 5/1990 |
| JP | 11-226109 * | 8/1999 |

* cited by examiner

*Primary Examiner*—Bernard Lipman
(74) *Attorney, Agent, or Firm*—Leydig, Voit & Mayer, Ltd.

(57) ABSTRACT

The present invention provides an adhesive tape or sheet for application to skin, which is made of an adhesive composition containing an acrylic copolymer having a specific composition and a specific carboxylic acid ester, wherein the acrylic copolymer has a gel fraction adjusted to a specific range. The adhesive tape or sheet for skin of the present invention can be used for first aid adhesive plasters, surgical tapes, large adhesive plasters with a pad, dressing materials and the like.

10 Claims, No Drawings

US 6,998,432 B2

ADHESIVE COMPOSITION FOR SKIN AND ADHESIVE TAPE OR SHEET FOR SKIN COMPRISING THE COMPOSITION

FIELD OF THE INVENTION

The present invention relates to an adhesive composition for application to skin, which is used for external application in the medical and sanitary fields, and to an adhesive tape or sheet for application to skin, which comprises this composition. The adhesive tape or sheet for application to skin is preferably used for first aid adhesive plasters and surgical tapes, large adhesive plasters with a pad, dressing materials and the like.

BACKGROUND OF THE INVENTION

An adhesive tape or sheet for application to skin generally has an adhesive layer formed on at least one surface of a substrate, and is adhered to the target skin surface via the adhesive layer. The adhesives used for an adhesive layer of such adhesive tape or sheet for application to skin are generally classified into rubber adhesives and acrylic adhesives.

A rubber adhesive is a composition containing a rubber component such as natural rubber, isoprene rubber, styrene/isoprene/styrene rubber and the like, and a tackifier, a softener and the like. This composition shows superior adhesion to a relatively dry skin surface. However, since rubber adhesives generally have high hydrophobicity and low moisture permeability, when an adhesive tape or sheet including this adhesive is applied to skin, the skin surface tends to get steamy due to sweat etc. to cause irritation to the skin. In summer, during sports and bathing when a lot of sweat is inevitable, moreover, the adhesion to the skin becomes radically poor.

An acrylic adhesive comprises a (meth)acrylic acid alkyl ester monomer as a main component monomer, and when copolymerized with various monomers, affords an adhesive having desired and well-balanced properties. Because control of the adhesive property is relatively easy, it is widely used as an adhesive layer of an adhesive tape or sheet for application to skin. Conventional acrylic adhesives relatively easily impart high hydrophilicity and high moisture permeability to an adhesive layer, thereby preventing steamy skin surfaces, but are inferior to rubber adhesives in adhesion to the skin. Conventional acrylic adhesives, like rubber adhesives, rapidly lose skin adhesiveness when exposed to much sweat in summer, during sports, bathing and the like.

Thus, the adhesive tapes or sheets for application to skin now in the market show superior adhesion to relatively dry skin surfaces, but once the skin surfaces get sweaty, cannot maintain the adhesiveness or sufficient adhesion to the skin.

Accordingly, there is a demand on an adhesive tape or sheet for application to skin that causes less steaminess of the skin surface and can show superior adhesion to the skin during perspiration.

An adhesive tape or sheet for application to skin may be required to secure adhesion to the skin surface for a long time, in addition to the capability of not causing steamy skin surface and adhesion during perspiration. To meet such requirements, the acrylic adhesive is crosslinked, gel content of the adhesive is carefully controlled, and skin adhesiveness and internal cohesion are balanced. When the gel content is too high, the internal cohesion becomes too high and the adhesive power to the skin decreases, as a result of which the adhesive tape or sheet for application to skin tends to become loose from the edge or come off easily.

An improved adhesion to the skin means a higher risk of intensifying irritation to the skin by peeling off of an adhesive from the skin. For the irritation upon peeling of an adhesive to be decreased, a liquid or paste of a plasticized component is added to the adhesive, and the adhesive is crosslinked to maintain the balance between high skin adhesive power and internal cohesion, thereby reducing the skin irritation.

In an attempt to solve the above-mentioned problems, there have been proposed a method including crosslinking an acrylic adhesive by ionization irradiation, thereby increasing the internal cohesion of an adhesive layer (JP-A-11-226109), and a method including addition of a liquid or paste of a plasticized component to an acrylic adhesive and crosslinking the acrylic adhesive by ionization irradiation, thereby decreasing skin irritation (U.S. Pat. No. 5,543,151). However, there is a risk that direct ionizing radiation of an acrylic adhesive may cause direct bonding of polymer chains of acrylic copolymer in the adhesive, which in turn causes too high an internal cohesion and intolerably low adhesion to the skin. When a plasticized component is contained in the acrylic adhesive, direct ionizing radiation for crosslinking makes it difficult to retain plasticized components between polymer chains, with the result of exudated plasticized component from the adhesive layer. In this event, the irritation to the skin cannot be decreased, and exudated plasticized component contaminates the skin, thereby possibly inducing even stronger irritation to the skin.

Thus, an adhesive tape or sheet for application to skin, which causes less steaminess of the skin surface, can show superior adhesion to the skin for a long time during perspiration, and which causes less irritation to the skin has been also demanded.

SUMMARY OF THE INVENTION

According to the present invention, it has been found that an adhesive tape or sheet for application to skin, which is made of an adhesive composition comprising an acrylic copolymer having a specific composition and a specific carboxylic acid ester, wherein the copolymer has a specific gel fraction, causes less steaminess of the skin surface and shows superior skin adhesion even during perspiration. It has been further found that an adhesive tape or sheet for application to skin, which is obtained by subjecting an adhesive tape or sheet for application to skin, which is made from an adhesive composition comprising an acrylic copolymer having a specific composition and a specific carboxylic acid ester, wherein the copolymer has a specific gel fraction, to ionization irradiation to increase and adjust the gel fraction of the acrylic copolymer to a specific range after irradiation causes less steaminess of the skin surface, shows superior skin adhesion for a long time even during perspiration and causes less irritation to the skin.

Accordingly, the present invention provides the following.

(1) An adhesive composition for application to skin, which comprises
   an acrylic copolymer (100 parts by weight) obtained from a monomer mixture comprising a (meth)acrylic acid alkyl ester monomer (40–80 wt %), an alkoxy group-containing ethylenically unsaturated monomer (10–60 wt %) and a carboxy group-containing ethylenically unsaturated monomer (1–10 wt %), and a carboxylic acid ester (20–120 parts by weight), which is liquid or paste at room temperature, wherein the acrylic copolymer has a gel fraction of 30–80 wt %;

(2) an adhesive tape or sheet for application to skin comprising the adhesive composition of the above-mentioned (1), which is formed in a layer directly or indirectly on at least one surface of a substrate;

(3) an adhesive composition for application to skin, which comprises an acrylic copolymer (100 parts by weight) obtained from a monomer mixture comprising a (meth)acrylic acid alkyl ester monomer (40–80 wt %), an alkoxy group-containing ethylenically unsaturated monomer (10–60 wt %) and a carboxy group-containing ethylenically unsaturated monomer (1–10 wt %) and a carboxylic acid ester (20–120 parts by weight), which is liquid or paste at room temperature, wherein the acrylic copolymer has a gel fraction of 20–60 wt %;

(4) an adhesive tape or sheet for application to skin, comprising the adhesive composition of the above-mentioned (3), which is formed in a layer directly or indirectly on at least one surface of a substrate;

(5) an adhesive tape or sheet for application to skin obtained by subjecting an adhesive tape or sheet for application to skin, which comprises the adhesive composition of the above-mentioned (3) formed in a layer directly or indirectly on at least one surface of a substrate, to ionization irradiation to increase and adjust the gel fraction of the acrylic copolymer in the adhesive layer to 30–80 wt % after irradiation; and (6) a method for producing an adhesive tape or sheet for application to skin, which method comprises the steps of a) obtaining an adhesive tape or sheet for application to skin by directly or indirectly forming a layer of the adhesive composition for application to skin of the above-mentioned (3) on at least one surface of a substrate, and b) subjecting the adhesive tape or sheet to ionization irradiation to increase and adjust the gel fraction of the acrylic copolymer in the adhesive layer to 30–80 wt % after irradiation.

DETAILED DESCRIPTION OF THE INVENTION

The adhesive tape or sheet for skin of the present invention comprises a substrate and a layer of an adhesive composition for application to skin, which is formed at least on one surface of the substrate. The adhesive composition characteristically contains an acrylic copolymer obtained from a monomer mixture of predetermined amounts of a (meth)acrylic acid alkyl ester monomer, an alkoxy group-containing ethylenically unsaturated monomer and a carboxy group-containing ethylenically unsaturated monomer, and a carboxylic acid ester, which is liquid or paste at room temperature, wherein the acrylic copolymer has a predetermined gel fraction.

A. Adhesive Composition for Application to Skin

A.1. Acrylic Copolymer

The acrylic copolymer to be used for the adhesive composition for application to skin according to the present invention is a copolymer obtained from a monomer mixture of a (meth)acrylic acid alkyl ester monomer, an alkoxy group-containing ethylenically unsaturated monomer, and a carboxy group-containing ethylenically unsaturated monomer as essential components. Each monomer is explained in detail in the following.

(Meth)Acrylic Acid Alkyl Ester Monomer

The (meth)acrylic acid alkyl ester monomer imparts adhesiveness (or skin adhesion property) to an adhesive layer. The adhesive layer made from a (meth)acrylic acid alkyl ester monomer is advantageous in that it causes relatively less irritation to the skin, and adhesion to the skin is not easily degraded by use for a long time.

Such (meth)acrylic acid alkyl ester monomer is exemplified by linear or branched alkyl ester having 2 or more, preferably 6 to 15, carbon atoms. Examples thereof include ethyl ester, propyl ester, butyl ester, pentyl ester, hexyl ester, heptyl ester, octyl ester, nonyl ester, decyl ester and dodecyl ester of acrylic acid or methacrylic acid and the like. These esters may be used alone or in combination of two or more thereof.

In the adhesive composition of the present invention, it is preferable that 40–80 wt %, preferably 50–70 wt %, of the above-mentioned (meth)acrylic acid alkyl ester monomer be copolymerized with various ethylenically unsaturated monomers to be mentioned later. When the amount of the (meth)acrylic acid alkyl ester monomer to be copolymerized is less than 40 wt %, the obtained acrylic copolymer does not show sufficient skin adhesion, whereas when it exceeds 80 wt %, the obtained acrylic copolymer shows decreased cohesion, which may result in an adhesive residue after peeling off thereof from the skin surface.

A.2. Alkoxy Group-containing Ethylenically Unsaturated Monomer

The alkoxy group-containing ethylenically unsaturated monomer imparts hydrophilicity to the acrylic copolymer to afford water vapor permeability and hygroscopicity of the adhesive layer. It is an essential component for the expression of the effect of the present invention.

As the alkoxy group-containing ethylenically unsaturated monomer, preferred is alkoxy alkyl acrylate or alkoxy polyethyleneglycol acrylate containing alkoxy having 1 to 4 carbon atoms. Examples thereof include methoxyethyl acrylate, ethoxyethyl acrylate, butoxyethyl acrylate, methoxy polyethyleneglycol acrylate, ethoxydiethyleneglycol acrylate, butoxydiethyleneglycol acrylate and the like.

The above-mentioned alkoxy group-containing ethylenically unsaturated monomer is desirably copolymerized and contained in the acrylic copolymer in a proportion of 10–60 wt %, preferably 20–50 wt %. When the amount of copolymerization is less than 10 wt %, sufficient hydrophilicity and skin adhesion necessary for the adhesive layer during perspiration cannot be afforded. When it exceeds 60 wt %, the adhesive shows poor skin adhesion of an impractical level.

A.3. Carboxy Group-containing Ethylenically Unsaturated Monomer

In the carboxy group-containing ethylenically unsaturated monomer, its carboxyl group acts as a reaction point in the cross linking treatment, and improves internal cohesion of the adhesive layer. This component is important for the preparation of an adhesive composition for application to skin according to the present invention.

Typical examples of such monomer include acrylic acid, methacrylic acid, itaconic acid, crotonic acid, fumaric acid, maleic acid (anhydride) and the like. Of these monomers, acrylic acid and methacrylic acid are preferable from the aspects of copolymerization performance, handling property and the like.

The above-mentioned carboxy group-containing ethylenically unsaturated monomer is copolymerized and contained in the acrylic copolymer in a proportion of about 1–10 wt %, preferably 3–8 wt %. When the amount to be copolymerized exceeds 10 wt %, the adhesive layer shows improved internal cohesion but also shows unpreferably stronger irritation to the skin.

According to the present invention, a modifier monomer to compensate for various properties such as hydrophilicity and the like, various monomers such as styrene, vinyl acetate, N-vinyl-2-pyrrolidone, 2-hydroxyethyl acrylate, 2-hydroxypropyl acrylate and the like may be copolymerized as necessary with acrylic copolymer.

The above-mentioned acrylic copolymer preferably has a glass transition temperature of not less than 180° K. and not more than 250° K. When the glass transition temperature is not less than 180° K. and not more than 250° K., the adhesive tape or sheet for application to skin shows sufficient adhesion to the skin.

The above-mentioned acrylic copolymer has a weight-average molecular weight of not more than 1,000,000, preferably 500,000–900,000. According to the present invention, the adhesive composition is subjected to a chemical crosslinking treatment to be mentioned later to adjust the gel fraction of the acrylic copolymer to a predetermined range. Alternatively, an adhesive composition after a chemical crosslinking treatment is processed to give an adhesive layer and the adhesive layer is subjected to ionization irradiation to adjust the gel fraction to a predetermined range, thereby adjusting the internal cohesion of the adhesive layer. Therefore, the adhesive composition before chemical crosslinking treatment preferably has lower internal cohesion, and for this end, the weight-average molecular weight is preferably not more than 1,000,000. When the adhesive composition before chemical crosslinking treatment has a weight-average molecular weight of an acrylic copolymer of above 1,000,000, the internal cohesion of the adhesive layer thus formed may be increased too high to impair adhesion to the skin.

The above-mentioned acrylic copolymer is obtained by radical polymerization. As the initiator of the radical polymerization, usable is a radical polymerization initiator generally used in this field. Examples thereof include peroxide compound, azo compound and the like. The process of radical polymerization is that generally used in this field, such as solution polymerization, emulsion polymerization, suspension polymerization and the like.

A.4. Carboxylic Acid Ester

The adhesive composition for application to skin according to the present invention contains carboxylic acid ester, which is liquid or paste at room temperature (25° C.). By dissolving such carboxylic acid ester and the above-mentioned acrylic copolymer in an adhesive layer, the elastic modulus of the adhesive layer in a micro-deformation area is lowered and the adhesiveness (or wettability) of the surface of the adhesive layer to the irregularities on the skin surface to be adhered to is improved, whereby the adhesive layer shows superior adhesion to the skin. The addition of such carboxylic acid ester also imparts superior perspiration resistant adhesiveness to the adhesive layer. The mechanism of this has not been elucidated, but it is postulated that, during perspiration, water present in the interface between the skin surface and the adhesive layer is absorbed into the adhesive layer by the surfactant-like action of the carboxylic acid ester, and combined with a plasticizing effect of the carboxylic acid ester, water can move easily in the adhesive layer and water that reached the substrate is easily dispersed to the outside in water vapor. As a result, adhesion to the skin can be maintained during perspiration. The addition of carboxylic acid ester to the adhesive layer reduces irritation and damage of corneum when the adhesive tape or sheet is peeled off from the skin surface, thereby decreasing the pain.

In the adhesive composition for application to skin according to the present invention, carboxylic acid ester needs to be liquid or paste at room temperature. Carboxylic acid ester, which is solid (e.g., wax) at room temperature, is hardly dispersed uniformly in an adhesive composition but shows low compatibility with the composition. Consequently, the adhesive layer may not permit adhesion to the skin or uniform adhesion to the skin, which is unpreferable in the present invention.

The carboxylic acid ester, which is liquid or paste at room temperature, preferably shows affinity for and compatibility with acrylic copolymer, as well as affinity for water produced during perspiration. Specific examples include esters of monohydric alcohols such as ethyl myristate, isopropyl myristate, isopropyl palmitate, butyl stearate, isopropyl isostearate, hexyl laurate, cetyl lactate, myristyl lactate, diethyl phthalate, octyldodecyl myristate, octyldodecyl oleate, hexyldecyl dimethyloctanoate, cetyl 2-ethylhexanoate, isocetyl 2-ethylhexanoate, stearyl 2-ethylhexanoate, dioctyl succinate and the like with carboxylic acid, and esters of polyhydric alcohols such as propylene glycol dicaprylate, propylene glycol dicaprate, propylene glycol diisostearate, glyceryl monocaprylate, glyceryl tricaprylate, glyceryl tri(2-ethylhexanoate), glyceryl tricaprate, glyceryl trilaurate, glyceryl triisostearate, glyceryl trioleate, trimethylolpropane tri(2-ethylhexanoate) and the like with carboxylic acid.

The above-mentioned carboxylic acid ester includes both saturated fatty acid ester and unsaturated fatty acid ester. For the prevention of oxidative degradation, saturated fatty acid ester is preferable, particularly saturated fatty acid ester having 8 to 10 carbon atoms is more preferable. Of the above-mentioned carboxylic acid esters, glycerine ester is preferable in view of small irritation to the skin and the economical aspects. Of the above-mentioned carboxylic acid esters, glycerine ester of saturated fatty acid having 8–10 carbon atoms is most preferable. Specific examples include triglyceryl caprylate, triglyceryl caprate and triglyceryl 2-ethylhexanoate.

When an unsaturated fatty acid ester is used from among the above-mentioned carboxylic acid esters, addition of an antioxidant known in this field to the adhesive layer is desirable, because the adhesive may not show the desired properties when its property is changed by oxidative degradation due to the oxygen in the atmosphere.

One or more of the above-mentioned carboxylic acid esters is(are) contained in the adhesive composition in a proportion of 20–120 parts by weight, preferably 30–100 parts by weight, per 100 parts by weight of the above-mentioned acrylic copolymer. When the amount of the carboxylic acid ester is less than 20 parts by weight, the adhesion to the sweat skin surface may become drastically poor. When it exceeds 120 parts by weight, the adhesive layer becomes too soft to cause lower adhesion to the skin even when the skin is not sweaty, and carboxylic acid ester may bloom from the adhesive layer, staining the skin surface.

A.5. Gel Fraction

In the adhesive composition of the present invention, the proportion of the insolubilized acrylic copolymer (a gel fraction) is 30–80 wt %, preferably 35–70 wt %, of the total weight of the acrylic copolymer.

As used herein, by the "insolubilized" is meant an ability to not dissolve in an organic solvent, specifically toluene. By the "gel fraction" is meant a value obtained by immersing a dry adhesive sample in toluene at normal temperature for 7 days, passing the mixture through a polytetrafluoroethylene membrane (manufactured by Nitto Denko Corporation, NTF membrane) having an average pore size of 0.2 μm to separate insoluble matters, weighing the sample after drying and calculating a ratio to the weight of a dry sample before immersion.

When the adhesive composition of the present invention has a gel fraction of less than 30 wt %, the adhesive layer formed has insufficient internal cohesion. As a result, the tape or sheet may be displaced during adhesion to the skin surface and the adhesive may remain when the tape or sheet is peeled off from the skin surface. On the other hand, when the insolubilization ratio exceeds 80 wt %, the internal cohesion becomes too high, making the adhesion to the skin extremely low and, as a result, the tape or sheet may be peeled off from the edge during adhesion to the skin surface or fall off from the skin surface.

According to the present invention, a chemical crosslinking treatment is applied to insolubilize the acrylic copolymer in the adhesive composition for adhesion to the skin and to adjust the gel fraction. The crosslinking agent to be used for the chemical crosslinking includes organic compound such as organic peroxide (e.g., benzoyl peroxide and the like), isocyanate compound (e.g., multifunctional isocyanate such as tolylene diisocyanate, hexamethylene diisocyanate and the like), organic metal salt, metal chelate compound (e.g., aluminum tris(acetyl acetonate), ethylacetoacetate aluminum diisopropylate and the like), metal alcoholate compound, epoxy compound (e.g., glycerine triglycidyl ether, triglycidyl isocyanurate and the like), primary amino compound and the like. In view of easy adjustment of crosslinking degree, easy addition and stability of pot life, organic peroxide, isocyanate compound, epoxy compound and metal chelate compound are preferable, and isocyanate compound and metal chelate compound are more preferable.

In the present invention, the gel fraction of the acrylic copolymer in the adhesive composition may be first adjusted to a predetermined value by the aforementioned chemical crosslinking, and the obtained adhesive composition is applied to at least one surface of a substrate to form an adhesive layer. The resulting adhesive tape or sheet is subjected to ionization irradiation for physical crosslinking to adjust the gel fraction of the acrylic copolymer in the adhesive layer to 30–80 wt %.

According to this method, chemical crosslinking of acrylic copolymer with a crosslinking agent results in gentle crosslinking while retaining a suitably free space between polymer chains, which ensures a large amount of carboxylic acid ester contained in the adhesive composition. This adhesive composition is then applied to at least one surface of a substrate to give an adhesive tape or sheet, and the tape or sheet is subjected to ionization irradiation for physical crosslinking. This directly binds polymer chains of the acrylic copolymer, and suitably enhances internal cohesion of the adhesive layer, as well as stable retention of the carboxylic acid ester in the adhesive layer. Consequently, the adhesive layer has appropriate adhesiveness to the skin and the irritation to the skin can be decreased.

When using this method, the gel fraction of the acrylic copolymer in the adhesive layer before ionization irradiation needs to be adjusted to 20–60 wt %, preferably 25–50 wt %. When the gel fraction before ionization irradiation is less than 20%, the internal cohesion of the adhesive layer after ionization irradiation does not become sufficiently high. In this case, the adhesive may be left on the skin surface or extruded from the side face of the adhesive tape or sheet to stain the skin. When the gel fraction before ionization irradiation exceeds 60 wt %, the internal cohesion of the adhesive layer after ionization irradiation may become too high. In this case, the adhesive layer may become too stiff, which in turn decreases adhesiveness to the skin to allow peeling off of the tape or sheet from the edge or falling off during adhesion to the skin surface.

For the ionization irradiation to be applied in the present invention, typical radiations, such as γ ray, electron beam, X ray and the like, are used. In view of safety and handling property, γ ray or electron beam is preferably used.

The dose of the above-mentioned ionizing radiation is 20–50 kGy, preferably 25–35 kGy. Ionization irradiation applied to the adhesive tape or sheet for application to skin provides crosslinking of the adhesive layer as well as sterilization thereof. For use in the medical and sanitary fields for adhesion to the skin as in the present invention, this method is highly convenient.

The adhesive composition for application to skin according to the present invention may contain various additives as necessary, such as plasticizers (e.g., polyhydric alcohol such as glycerine, polyethylene glycol, polypropylene glycol etc. and the like), water soluble or water absorptive resins (e.g., polyacrylic acid, crosslinked polyacrylic acid, polyvinylpyrrolidone and the like), tackifier resins (e.g., rosin resin, terpene resin, petroleum resin and the like), various softeners, various fillers, pigments and the like, as long as the property of the composition is not impaired.

The above-mentioned adhesive composition is applied to at least one surface of a substrate to be mentioned later to give an adhesive layer having a thickness of 10–80 μm, preferably 10–60 μm. When the thickness is less than 10 μm, sufficient adhesion to the skin may not be secured, and when the thickness exceeds 80 μm, the adhesive tape or sheet as a whole cannot provide sufficient water vapor permeation, which means adhesion standing the sweat is difficult to achieve, and adhesion for a long time leads to steaminess which may cause irritation to the skin.

B. Substrate

The substrate constituting the adhesive tape or sheet for skin of the present invention is not subject to any particular limitation as long as it can support the adhesive layer. To markedly improve steaminess of the skin surface when the adhesive tape or sheet is adhered to the skin surface and to prevent degraded adhesion to the skin during perspiration, the use of a moisture permeable substrate is preferable.

The material of such substrate include urethane polymer (e.g., polyether polyurethane, polyester polyurethane and the like), amide polymer (e.g., polyether polyamide block copolymer and the like), acrylic polymer (e.g., polyacrylate and the like), polyolefin polymer (e.g., polyethylene, polypropylene, ethylene/vinyl acetate copolymer and the like), polyester polymer (e.g., polyether polyester copolymer and the like), cloth (e.g., nonwoven fabric) and the like. Of these, nonwoven fabric, urethane polymer and amide polymer are preferable, because they are particularly superior in water vapor permeation when prepared into an adhesive tape or sheet for application to skin and free of steaminess, whitening and the like when adhered to the skin surface. The substrate may be a monolayer film made of any one of the above-mentioned materials, or a laminate film consisting of plural films made of a single material or two or more kinds of materials.

The above-mentioned substrate has a thickness of 10–100 μm, preferably 20–40 μm, so that uncomfortableness is not felt at the site where the adhesive tape or sheet for application to skin is adhered.

It is also preferable to adjust the above-mentioned substrate to have a tensile strength of 100–900 kg/cm$^2$ and 100% modulus of 10–100 kg/cm$^2$, to provide fine skin-followability of the adhesive tape or sheet for application to skin. When a substrate having a tensile strength and a 100% modulus adjusted to these ranges is used for the adhesive tape or sheet for application to skin, it shows superior skin-followability even when applied to the joint where movement is frequent and greater.

As the substrate, both a non-porous film and a porous film may be used. A porous film is superior in water vapor permeation and can decrease steaminess more effectively when an adhesive tape or sheet for application to skin is adhered to the skin surface. When a porous film is to be used as a substrate, any material can be used as long as it can be processed into a porous film by a known technique for making the film porous. Preferred is a porous film made from a polyolefin resin, for example, polyethylene, polypropylene, ethylene/vinyl acetate copolymer and the like. Particularly, a porous film made from a linear low density polyethylene resin is preferable from the aspect of productivity and processability. As used herein, by the "linear low density polyethylene resin" is meant a polyethylene resin comprising a copolymer of ethylene and α-olefin as a main component and having a low density, wherein the α-olefin to be contained is exemplified by butene, hexene, octene and the like.

A non-porous film having a greater film thickness tends to show noticeably lower water vapor permeation. In contrast, a porous film having a greater film thickness does not show a noticeable decrease in water vapor permeation, and therefore, is useful in application requiring relatively greater thickness. For example, when the adhesive tape or sheet for skin of the present invention is used for an adhesive plaster having a relatively great thickness (generally about 100 μm), such as a first aid adhesive plaster, large adhesive plaster and the like, a porous film is preferably used as a substrate.

The adhesive tape or sheet for skin of the present invention preferably shows water vapor permeation. To be specific, the water vapor permeability of the adhesive tape or sheet as a whole is not less than 300 g/m$^2$·24 h·40° C.·30% R.H., preferably 300–2400 g/m$^2$·24 h·40° C.·30% R.H., more preferably 800–2400 g/m$^2$·24 h·40° C.·30% R.H. The lower limit of the water vapor permeability is set to 300 g/m$^2$·24 h·40° C.·30% R.H., because application of an adhesive tape or sheet having lower vapor permeability than this level to a human skin surface where perspiration is profuse, though subject to interindividual differences, prevents sufficient moisture permeability and unavoidably causes steaminess.

The adhesive tape or sheet for skin of the present invention generally has a release sheet temporarily set on the exposed surface of the adhesive layer. As a release sheet, any sheet known in this field can be used, such as a release sheet having a silicone-treated surface by a release treatment, and the like.

The present invention is explained in more detail in the following by referring to Examples. The present invention is not limited by these examples, but can be modified in many ways as long as they are within the scope not deviating from the technical conception of the present invention. In the following, "parts" means "parts by weight" and "%" means "wt %".

EXAMPLE 1

A monomer mixture containing isononyl acrylate (65 parts), 2-methoxyethyl acrylate (30 parts) and acrylic acid (5 parts) was uniformly mixed in toluene (80 parts) under an inert gas atmosphere. As a polymerization initiator, azobisisobutyronitrile (0.3 part) was added to carry out copolymerization to give an acrylic copolymer. The obtained acrylic copolymer had a Tg of 214° K. This copolymer (100 parts), triglyceryl caprylate (60 parts) as carboxylic acid ester and trifunctional isocyanate compound (0.1 part, CORONATE HL, manufactured by Nippon Polyurethane Industry Co., Ltd.) as a cross linking agent were mixed in toluene to give an adhesive composition. This composition was applied to a release sheet on the side that underwent a silicone treatment, so that the thickness after drying would be 40 μm, and dried by heating at 110° C. for 3 min to give an adhesive layer for the skin. A polyester nonwoven fabric (Sontara 8010, manufactured by Du Pont Company) was press adhered to the surface of the obtained adhesive layer. Aging at 60° C. for 72 h gave the adhesive sheet for adhesion to the skin of the present invention.

EXAMPLE 2

In the same manner as in Example 1 except that the amount of triglyceryl caprylate was 30 parts, the adhesive sheet for adhesion to the skin of the present invention was prepared.

EXAMPLE 3

In the same manner as in Example 1 except that the amount of triglyceryl caprylate was 100 parts and the amount of trifunctional isocyanate compound was 0.14 part, the adhesive sheet for adhesion to the skin of the present invention was prepared.

EXAMPLE 4

In the same manner as in Example 1 except that, as carboxylic acid ester, isopropyl myristate (50 parts) was used instead of triglyceryl caprylate (60 parts), and the amount of trifunctional isocyanate compound was 0.12 part, the adhesive sheet for adhesion to the skin of the present invention was prepared.

EXAMPLE 5

In the same manner as in Example 1 except that the adhesive composition contained isononyl acrylate (70 parts), 2-ethoxyethyl acrylate (25 parts) and acrylic acid (5 parts), the adhesive sheet for adhesion to the skin of the present invention was prepared.

Comparative Example 1

In the same manner as in Example 1 except that the triglyceryl caprylate was not added, the adhesive sheet for adhesion to the skin of Comparative Example was prepared.

Comparative Example 2

In the same manner as in Example 1 except that, as an acrylic copolymer, a copolymer obtained by copolymerization of a monomer mixture containing 2-ethylhexyl acrylate (92 parts) and acrylic acid (8 parts) was used and the amount of trifunctional isocyanate compound was set to 0.11 part, the adhesive sheet for adhesion to the skin of Comparative Example was prepared.

Comparative Example 3

In the same manner as in Example 1 except that, as an acrylic copolymer, a copolymer obtained by copolymerization of a monomer mixture containing 2-ethylhexyl acrylate (70 parts) and 2-methoxyethyl acrylate (30 parts) was used and trifunctional isocyanate compound was not added, the adhesive sheet for adhesion to the skin of Comparative Example was prepared.

Comparative Example 4

In the same manner as in Example 1 except that polyethylene glycol (60 parts, molecular weight 400) was used instead of triglyceryl caprylate and the amount of trifunctional isocyanate compound was 0.16 part, the adhesive sheet for adhesion to the skin of Comparative Example was prepared.

Comparative Example 5

In the same manner as in Example 1 except that the amount of trifunctional isocyanate compound was 0.05 part, the adhesive sheet for adhesion to the skin of Comparative Example was prepared.

Comparative Example 6

In the same manner as in Example 1 except that the amount of trifunctional isocyanate compound was 0.40 part, the adhesive sheet for adhesion to the skin of Comparative Example was prepared.

Comparative Example 7

A styrene/isoprene/styrene block copolymer (30 parts, styrene content 15%), liquid polyisoprene (30 parts) and β-pinene polymer (40 parts, softening point 115° C.) were uniformly mixed in toluene, and the mixture was applied to a silicone-treated surface of a release sheet in the same manner as in Example 1, and dried to give an adhesive sheet for adhesion to the skin of Comparative Example.

Comparative Example 8

In the same manner as in Example 1 except that the amount of triglyceryl caprylate was 15 parts, the adhesive sheet for adhesion to the skin of Comparative Example was prepared.

Comparative Example 9

In the same manner as in Example 1 except that the amount of triglyceryl caprylate was 140 parts and the amount of trifunctional isocyanate compound was 0.12 part, the adhesive sheet for adhesion to the skin of Comparative Example was prepared.

EXAMPLE 6

A monomer mixture containing isononyl acrylate (65 parts), 2-methoxyethyl acrylate (30 parts) and acrylic acid (5 parts) was uniformly mixed in toluene (80 parts), and as a polymerization initiator, azobisisobutyronitrile (0.3 part) was added to conduct copolymerization. The obtained acrylic copolymer (100 parts), triglyceryl caprylate (60 parts) as carboxylic acid ester and trifunctional isocyanate compound (0.1 part, CORONATE HL, manufactured by Nippon Polyurethane Industry Co., Ltd.) as a cross linking agent were mixed in toluene to give an adhesive composition. This composition was applied to a release sheet on the side that underwent a silicone treatment, so that the thickness after drying would be 30 μm, and dried by heating at 110° C. for 3 min to give an adhesive layer. The prepared adhesive layer was placed on one side of a polyether polyurethane film (thickness 25 μm) and adhered, which was followed by aging at 60° C. for 72 h. After the aging, 25 kGy γ ray was irradiated on the adhesive layer to give the adhesive sheet for adhesion to the skin of the present invention.

EXAMPLE 7

In the same manner as in Example 6 except that triglyceryl caprate was used instead of triglyceryl caprylate, the adhesive sheet for adhesion to the skin of the present invention was prepared.

EXAMPLE 8

In the same manner as in Example 6 except that ethylacetoacetate aluminum diisopropylate (metal chelate compound) was used instead of trifunctional isocyanate compound as a cross linking agent, the adhesive sheet for adhesion to the skin of the present invention was prepared.

Comparative Example 10

In the same manner as in Example 6 except that, after adhering adhesive layer formed on a release sheet on one side of a polyether polyurethane film, the aging was not performed, the adhesive sheet for adhesion to the skin of Comparative Example was prepared.

Comparative Example 11

In the same manner as in Example 6 except that the amount of trifunctional isocyanate compound was changed from 0.1 part to 0.3 part, the adhesive sheet for adhesion to the skin of Comparative Example was prepared.

Comparative Example 12

In the same manner as in Example 6 except that the amount of triglyceryl caprylate was changed from 60 parts to 15 parts, the adhesive sheet for adhesion to the skin of Comparative Example was prepared.

Comparative Example 13

In the same manner as in Example 6 except that the amount of triglyceryl caprylate was changed from 60 parts to 140 parts, the adhesive sheet for adhesion to the skin of Comparative Example was prepared.

Comparative Example 14

In the same manner as in Example 6 except that triglyceryl caprylate was not added, the adhesive sheet for adhesion to the skin of Comparative Example was prepared.

Comparative Example 15

In the same manner as in Example 6 except that trifunctional isocyanate compound was not added, the adhesive sheet for adhesion to the skin of Comparative Example was prepared.

Comparative Example 16

In the same manner as in Example 6 except that, after adhering adhesive layer formed on a release sheet on one side of a polyether polyurethane film, the aging and γ ray irradiation were not performed, the adhesive sheet for adhesion to the skin of Comparative Example was prepared.

Test Method 1

The adhesive sheets for adhesion to the skin obtained in the above-mentioned Examples 1 to 5 and Comparative Examples 1 to 9 were subjected to the following tests, the results of which are shown in Table 1.

Measurement of Gel Fraction

A predetermined amount (ca. 0.2 g) of the adhesive of each adhesive sheet of Examples 1 to 5 and Comparative Examples 1 to 9 was taken, and weighed [weight (W1)]. The adhesive was immersed in toluene at normal temperature for 7 days and soluble components were extracted. Insoluble matters (residue) were filtered through a polytetrafluoroethylene membrane (average pore size 0.2 μm, NTF membrane, manufactured by Nitto Denko Corporation), dried and weighed [weight (W2)]. The ratio of the insoluble matter (gel fraction) was calculated from the following formula.

$$\text{Gel fraction } (\%) = [W2/(W1 \times A/B)] \times 100$$

A=weight (g) of (acrylic copolymer+cross linking agent)

B=weight (g) of (acrylic copolymer+cross linking agent+carboxylic acid ester+other additive)

Water Vapor Permeability

Distilled water (10 ml) was placed in a glass container (inner diameter 40 mm, height 40 mm), an adhesive sheet for adhesion to the skin cut in a 50 mm diameter circle was adhered to the mouth of the container with the adhesive layer facing downward and fixed. The weight (W3) of the container, to which the adhesive sheet was adhered, was measured and the container was placed in a thermo-hygrostat set at 40° C. and relative humidity 30% R.H., and a weight (W4) was measured 24 h later. The water vapor permeability was calculated from the following formula.

$$\text{Water vapor permeability } (g/m^2 \cdot 24 \text{ h} \cdot 40° \text{ C.} \cdot 30\% \text{ R.H.}) = (W3 - W4)/(0.02 \times 0.02 \times \pi)$$

Adhesion to the Skin (Normal State)

In a laboratory set to the thermo-hygrostat conditions at 23° C. and relative humidity of 60% R.H., an adhesive sheet for adhesion to the skin cut in a 20 mm×60 mm rectangular shape was press adhered to the back of a volunteer, who had rested for not less than 30 min, by one reciprocation with a 2 kg roller, and the adhesive sheet was peeled off after 20 min at a peeling rate of 300 mm/min in the 180 degree direction. The peel resistance stress then was taken as adhesion to the skin (normal state).

Adhesion to the Skin (Perspiration)

In a laboratory set to the thermo-hygrostat conditions at 23° C. and relative humidity of 60% R.H., an adhesive sheet for adhesion to the skin cut in a 20 mm×60 mm rectangular shape was press adhered to the back of a volunteer, who had rested for not less than 30 min, by one reciprocation with a 2 kg roller. The part, where the adhesive sheet was adhered, was sealed with a polyester film (water vapor permeability 10 g/m·24 h·40° C.·30% R.H. or less), and after 6 h, the adhesive sheet was peeled at a rate of 300 mm/min in the 180 degree direction. The peel resistance stress then was taken as the adhesion to the skin (perspiration).

Adhesive Residue Upon Peeling

The adhesion to the skin at normal state and during perspiration as mentioned above was measured and the skin surface thereafter was visually observed to judge the presence of an adhesive residue on the skin surface according to the following criteria.

○: no adhesive residue on the skin surface

Δ: partial adhesive residue on the skin surface x: adhesive residue on the entirety of the skin surface

Maceration of Skin Surface Upon Peeling

After the test of adhesion to the skin during perspiration, the skin surface was visually observed, and the degree of maceration of the skin surface was evaluated according to the following criteria.

○: maceration was not found, same as the surrounding skin

Δ: slightly macerated white, different from the surrounding skin x: apparently macerated white

TABLE 1

| | | Gel fraction (%) | Water vapor permeability (g/m²) | Adhesion to skin (N/20 mm) | | Adhesive residue upon peeling | | Maceration just after peeling |
|---|---|---|---|---|---|---|---|---|
| | | | | Normal state | Perspiration | Normal state | Perspiration | |
| Ex. | 1 | 48 | 1320 | 1.19 | 1.12 | ○ | ○ | ○ |
| | 2 | 54 | 970 | 1.25 | 1.16 | ○ | ○ | ○ |
| | 3 | 62 | 1350 | 1.02 | 0.94 | ○ | ○ | ○ |
| | 4 | 55 | 1270 | 0.98 | 0.81 | ○ | ○ | ○ |
| | 5 | 52 | 870 | 1.04 | 0.99 | ○ | ○ | ○ |
| Com. Ex. | 1 | 45 | 820 | 1.50 | 0.48 | ○ | ○ | ○ |
| | 2 | 55 | 630 | 0.75 | 0.98 | ○ | ○ | Δ |
| | 3 | 15 | 740 | 0.50 | 0.32 | ○ | ○ | ○ |
| | 4 | 50 | 1050 | 0.25 | fell | ○ | —*1 | ○ |
| | 5 | 22 | —*2 | 2.33 | 1.86 | X | X | ○ |
| | 6 | 87 | 1290 | 0.42 | 0.65 | ○ | ○ | ○ |
| | 7 | 0 | 70 | 0.46 | 0.24 | ○ | ○ | X |
| | 8 | 58 | 920 | 1.39 | 0.62 | ○ | ○ | ○ |
| | 9 | 51 | 1480 | 0.44 | 0.65 | ○ | ○ | ○ |

Note *1: judgment not possible due to falling off of adhesive sheet
*2: judgment not possible because uniform adhesive layer was not formed As is evident from the results shown in the above-mentioned Table 1, the adhesive sheets of Examples 1–5 showed smaller difference between the adhesion to the skin in normal state and the adhesion to the skin during perspiration, as compared to the adhesive sheets of Comparative Examples 1–9, and were superior in the adhesion to the skin during perspiration. In addition, the adhesive sheets of Examples 1–5 showed no adhesive residue upon peeling or maceration of the skin.

Test Method 2

The adhesive sheets for adhesion to the skin obtained in the above-mentioned Examples 6 to 8 and Comparative Examples 10 to 16 were subjected to the following tests, the results of which are shown in Table 2.

Gel Fraction

In the same manner as in Test method 1, gel fraction of each adhesive sheet was calculated.

Adhesion to the Skin

Each adhesive sheet for adhesion to the skin was adhered to the back of volunteers, and after 24 h, the adhesion to the skin was visually evaluated according to the following criteria.
○: No peeling
x: Peeling of the edge or falling off Irritation to the Skin After adhesion for 24 h in the above-mentioned test of adhesion to the skin, the adhesive sheet for adhesion to the skin was peeled off from the back of the volunteers. The irritation to the skin was evaluated based on the pain upon peeling according to the following criteria.
603 : No pain upon peeling or slight pain was perceived but was not disturbing.
x: Presence of pain at a disturbing level.

Internal Cohesion

The adhesive layer and the skin surface were visually observed during the above-mentioned test of the adhesion to the skin, and during peeling off thereof from the back after the test, based on which the internal cohesion of the adhesive layer was evaluated according to the following criteria.
○: No occurrence of protrusion of adhesive layer from the side face of the adhesive sheet for adhesion to the skin during the test, dislocation of adhesion site during the test, or adhesive residue on the skin surface upon peeling.
x: Occurrence of protrusion of adhesive layer from the side face of the adhesive sheet for adhesion to the skin during the test, dislocation of adhesion site during the test, or adhesive residue on the skin surface upon peeling.

TABLE 2

| | Gel fraction (%) | | | | |
| | Before γ ray irradiation | After γ ray irradiation | Skin adhesion | Irritation to skin | Internal cohesion |
| --- | --- | --- | --- | --- | --- |
| Ex. 6 | 40 | 56 | ○ | ○ | ○ |
| Ex. 7 | 31 | 48 | ○ | ○ | ○ |
| Ex. 8 | 25 | 46 | ○ | ○ | ○ |
| Com. Ex. 10 | 0 | 40 | ○ | X | ○ |
| Com. Ex. 11 | 67 | 83 | X | ○ | ○ |
| Com. Ex. 12 | 48 | 62 | ○ | X | ○ |
| Com. Ex. 13 | 42 | 58 | X | ○ | ○ |
| Com. Ex. 14 | 50 | 64 | ○ | X | ○ |
| Com. Ex. 15 | 0 | 12 | ○ | X | X |
| Com. Ex. 16 | 0 | — | ○ | X | X |

According to the present invention, an adhesive composition comprising an acrylic copolymer having a specific composition and a specific carboxylic acid ester, wherein the copolymer has a specific gel fraction, is used to provide an adhesive tape or sheet for application to skin, which causes reduced steaminess of the skin surface, which is capable of affording superior adhesion to the skin during perspiration and for a long time, and which is associated with less irritation to the skin. According to the present invention, the above-mentioned adhesive tape or sheet for application to skin is subjected to ionization irradiation to increase the gel fraction, thereby to adjust the gel fraction of the acrylic copolymer in the adhesive layer to a specific range after irradiation. As a result, an adhesive tape or sheet for application to skin is provided, which causes reduced steaminess of the skin surface, is capable of affording superior adhesion to the skin during perspiration and for a long time, and which is associated with less irritation to the skin.

This application is based on patent application Nos. 2000-265365 and 20001-121313 filed in Japan, the contents of which are hereby incorporated by reference.

What is claimed is:

1. An adhesive composition for application to skin, which comprises
    an acrylic copolymer (100 parts by weight) obtained from a monomer mixture comprising a (meth)acrylic acid alkyl ester monomer (40–80 wt %), an alkoxy group-containing ethylenically unsaturated monomer (10–60 wt %) and a carboxy group-containing ethylenically unsaturated monomer (1–10 wt %), and
    a triglycerine ester of a saturated fatty acid having 8 to 10 carbon atoms (20–120 parts by weight), which is liquid or paste at room temperature,
    wherein the acrylic copolymer has a gel fraction of 30–80 wt %.

2. The adhesive composition for application to skin according to claim 1, wherein the saturated fatty acid having 8 to 10 carbon atoms is selected from the group consisting of a caprylic acid, a capric acid and a 2-ethylhexanoic acid.

3. The adhesive composition for application to skin according to claim 1, wherein the triglycerine ester of saturated fatty acid is selected from the group consisting of triglyceryl caprylate, triglyceryl caprate and triglyceryl 2-ethylhexanoate.

4. The adhesive composition for application to skin according to claim 1, wherein the adhesive composition is chemically crosslinked.

5. The adhesive composition for application to skin according to claim 4, wherein the chemical crosslinking is performed using an organic compound selected from the group consisting of an organic peroxide, an isocyanate compound, an epoxy compound and a metal chelate compound.

6. An adhesive composition for application to skin comprising
an acrylic copolymer (100 parts by weight) obtained from a monomer mixture comprising a (meth)acrylic acid alkyl ester monomer (40–80 wt %), an alkoxy group-containing ethylenically unsaturated monomer (10–60 wt %) and a carboxy group-containing ethylenically unsaturated monomer (1–10 wt %) and
a triglycerine ester of a saturated fatty acid having 8 to 10 carbon atoms (20–120 parts by weight), which is liquid or paste at room temperature,
wherein the acrylic copolymer has a gel fraction of 20–60 wt %.

7. The adhesive composition for application to skin according to claim 6, wherein the saturated fatty acid having 8 to 10 carbon atoms is selected from the group consisting of a caprylic acid, a capric acid and a 2-ethylhexanoic acid.

8. The adhesive composition for application to skin according to claim 6, wherein the triglycerine ester of saturated fatty acid is selected from the group consisting of triglyceryl caprylate, triglyceryl caprate and triglyceryl 2-ethylhexanoate.

9. The adhesive composition for application to skin according to claim 6, wherein the adhesive composition is chemically crosslinked.

10. The adhesive composition for application to skin according to claim 9, wherein the chemical crosslinking is performed using an organic compound selected from the group consisting of an organic peroxide, an isocyanate compound, an epoxy compound and a metal chelate compound.

* * * * *